US012797349B2

(12) United States Patent
Jing et al.

(10) Patent No.: US 12,797,349 B2
(45) Date of Patent: Nov. 17, 2026

(54) USE OF METHYLAMINOCOLCHICINE AND SALT THEREOF

(71) Applicant: Shenyang Pharmaceutical University, Shenyang (CN)

(72) Inventors: Yongkui Jing, Shenyang (CN); Juanjuan Yang, Shenyang (CN); Dake Song, Shenyang (CN); Yuetong Wang, Shenyang (CN); Guoliang Chen, Shenyang (CN)

(73) Assignee: Shenyag Pharmaceutical University (CN)

( * ) Notice: Subject to any disclaimer, the term of this patent is extended or adjusted under 35 U.S.C. 154(b) by 450 days.

(21) Appl. No.: 18/475,312

(22) Filed: Sep. 27, 2023

(65) Prior Publication Data

US 2024/0238223 A1 Jul. 18, 2024

(30) Foreign Application Priority Data

Jan. 6, 2023 (CN) ........................ 202310018497.9

(51) Int. Cl.
*A61K 31/165* (2006.01)
*A61K 45/06* (2006.01)
*A61P 35/00* (2006.01)

(52) U.S. Cl.
CPC ............ *A61K 31/165* (2013.01); *A61K 45/06* (2013.01); *A61P 35/00* (2018.01)

(58) Field of Classification Search
CPC .... A61K 31/165; A61K 45/06; A61K 31/337; A61K 2300/00; A61P 35/00; A61P 35/02
USPC .......................................................... 514/617
See application file for complete search history.

(56) References Cited

U.S. PATENT DOCUMENTS

2011/0008372 A1* 1/2011 Chen .................... A61K 31/704 514/183

OTHER PUBLICATIONS

Krzywik, Julia et al. "New Series of Double-Modified Colchicine Derivatives: Synthesis, Cytotoxic Effect and Molecular Docking." Molecules (Basel, Switzerland) vol. 25, 15 3540. Aug. 2, 2020 (Year: 2020).*

(Continued)

*Primary Examiner* — James H Alstrum-Acevedo
*Assistant Examiner* — Sahar Inam
(74) *Attorney, Agent, or Firm* — Adam K. Sacharoff; Much Shelist, P.C.

(57) ABSTRACT

The present disclosure relates to the field of tumor drug therapy, in particular to use of a methylaminocolchicine and salts thereof. The use includes use of a methylamino-substituted colchicine at C10 position and salts thereof in preparation of antitumor drugs, use thereof in antitumor drugs for antagonizing microtubule inhibitor resistance, or use thereof in combination an antitumor drug. In the present disclosure, the methylaminocolchicine and the salts thereof have significant antitumor effects, are more active than paclitaxel, vincristine, and colchicine, do not exhibit cross resistance to the paclitaxel and the vincristine, and inhibit paclitaxel-resistant cell growth in vivo. With in vivo acceptable therapeutic indexes, the methylaminocolchicine and the salts thereof have a synergistic antitumor effect when used in combination with an anti-apoptotic protein Bcl-2/Bcl-xL inhibitor.

4 Claims, 4 Drawing Sheets

(56) References Cited

OTHER PUBLICATIONS

Yang et al. Replacing the tropolonic methoxyl group of colchicine with methylamino increases tubulin binding affinity with improved therapeutic index and overcomes paclitaxel cross-resistance, Drug Resistance Updates, vol. 68, May 2023, 100951 (Year: 2023).*
Hanahan et al. "The Hallmarks of Cancer." Cell, vol. 100, Jan. 7, 2000 (Year: 2000).*
Jordan, M., Wilson, L. "Microtubules as a target for anticancer drugs", Nature Reviews Cancer, vol. 4, 253-265, Apr. 1, 2004.*

* cited by examiner

USE OF METHYLAMINOCOLCHICINE AND SALT THEREOF

CROSS REFERENCE TO RELATED APPLICATION

This patent application claims the benefit and priority of Chinese Patent Application No. 202310018497.9, filed with the China National Intellectual Property Administration on Jan. 6, 2023, the disclosure of which is incorporated by reference herein in its entirety as part of the present application.

TECHNICAL FIELD

The present disclosure relates to the field of tumor drug therapy, in particular to use of a methylaminocolchicine and salts thereof.

BACKGROUND

Microtubule inhibitors play an important role in tumor therapy. There are two major groups of microtubule inhibitors used in current clinical setting: taxane and vinca alkaloids binding site inhibitors. Taxane binding site inhibitors (paclitaxel and semi-synthetic doctaxel) and vinca alkaloids binding site inhibitors (vincristine and vinblastine) are used in first-line chemotherapy for solid tumors and leukemia. Drug resistance is the major reason of therapy failure in clinical use. Currently revealed resistance mechanisms include P-glycoprotein (P-gp)-induced transport and excretion, increased drug metabolism, changes in expression levels of β-tubulin subtypes, mutation, and apoptosis evasion. Overcoming drug resistance and enhancing efficacy is the key to improve the clinical therapeutic effect of tubulin inhibitors on tumors.

Colchicine is an alkaloid derived from *Colchicum autumnale* of the family Liliaceae. In 2009, colchicine was approved by the U.S. Food and Drug Administration (FDA) for treating acute gout and familial Mediterranean fever (FMF) and for preventing gouty arthritis. Although colchicine exhibits strong inhibitory activity in tumor cell lines, it has not been approved by FDA for tumor therapy due to its weak in vivo efficacy and narrow toxicity index.

Structurally modified compounds of colchicine have been reported, but no compounds have been approved for tumor therapy yet due to the selection of activity and toxicity. So far, the inhibitory activity of methylaminocolchicine and its salts against paclitaxel- and vincristine-resistant tumors and combination therapies of them with anti-apoptotic protein Bcl-2/Bcl-xL inhibitor have not been reported yet.

SUMMARY

To overcome technical defects in the prior art, the present disclosure provides a preparation method of a methylaminocolchicine and salts thereof, which are used to overcome microtubule inhibitor resistance and used for combination therapies for various hematological malignancies and solid tumors when used in combination with an anti-apoptotic protein Bcl-2/Bcl-xL inhibitor.

Use of a methylaminocolchicine and salts thereof is provided, including use of a methylamino-substituted colchicine at C10 position and salts thereof in preparation of antitumor drugs, use thereof in antitumor drugs for antagonizing microtubule inhibitor resistance, or use thereof in combination with antitumor drugs for treating microtubule inhibitor resistance.

Tumor cells include human leukemia cells HL-60, K562, and MOLM-13, prostate cancer cells PC-3, hepatoma cells HepG-2, colon cancer cells HCT-116, and cervical cancer cells Hela, but are not limited to above cells.

Use of the methylaminocolchicine and the salts thereof in preparation of drug-resistant tumors for antagonizing microtubule inhibitor resistance (the antitumor microtubule inhibitor may include paclitaxel, semi-synthetic doctaxel, vincristine, and vinblastine) is provided.

Drug-resistant tumor cells include human non-small cell lung cancer (NSCLC) A549 cells and paclitaxel-resistant A549/T cells, human breast cancer MCF-7 cells and paclitaxel-resistant MCF-7/T cells, human breast cancer MX-1 cells and paclitaxel-resistant MX-1/T cells, and human oral epidermoid carcinoma KB cells and vincristine-resistant KB/V cells, but are not limited to above cells.

Use of the methylaminocolchicine and the salts or the methylaminocolchicine and the salts thereof in combination with an anti-apoptotic protein Bcl-2/Bcl-xL inhibitor (the anti-apoptotic protein Bcl-2/Bcl-xL inhibitor may include venetoclax, navitoclax, A1331852, and A1155463) as microtubule inhibitor resistant and non-resistant tumors is provided.

The tumors may include hematological malignancies and solid tumors.

The hematological malignancies may include leukemia and lymphoma; and the solid tumors may include breast cancer, lung cancer, prostate cancer, liver cancer, renal cancer, colon cancer, gastric cancer, and skin cancer.

The methylaminocolchicine is represented by Formula I:

Formula I

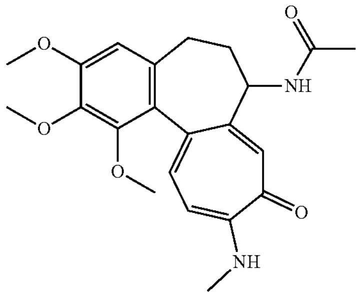

the salts of the methylaminocolchicine are represented by Formula II:

Formula II

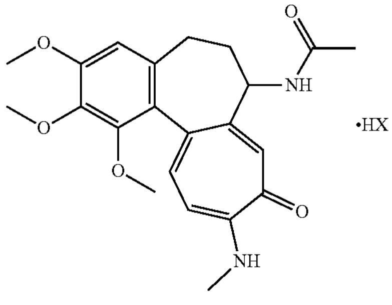

•HX where HX includes, but is not limited to, one selected from the group consisting of hydrochloric acid, hydrobromic acid, nitric acid, sulfuric acid, phosphoric acid, sulfamic acid, trifluoroacetic acid, acetic acid, benzoic acid, methanesulfonic acid, phenylacetic acid, salicylic acid, oxalic acid, maleic acid, malic acid, fumaric acid, succinic acid, tartaric acid, lactic acid, gluconic acid, hydroxymaleic acid, and 1,4-butanedisulfonic acid.

The methylaminocolchicine and the salts thereof are in the pharmaceutical dosage form of a tablet, a capsule, a granule, and an injection.

The methylaminocolchicine and the salts thereof in a pharmaceutical composition of the methylaminocolchicine and the salts thereof may be used concomitantly with the Bcl-2/Bcl-xL inhibitor or in any order of priority.

The methylaminocolchicine and the salts thereof in the pharmaceutical composition of the methylaminocolchicine and the salts thereof, a pharmaceutical composition of a Bcl-2/Bcl-xL inhibitor, and pharmaceutically acceptable carriers or vehicles are formulated into a clinically acceptable compound preparation.

For the methylaminocolchicine and the salts thereof in the pharmaceutical composition of the methylaminocolchicine and the salts thereof and the pharmaceutical composition of the Bcl-2/Bcl-xL inhibitor, components of the methylaminocolchicine and the salts thereof and the Bcl-2/Bcl-xL inhibitor in the composition may be mixed in a molar ratio of 1:250 to 1:1,000. Preferably, the components of the methylaminocolchicine and the salts thereof and the Bcl-2/Bcl-xL inhibitor may be mixed in a molar ratio of 1:250.

The present disclosure has the following advantages:

In the present disclosure, the methylaminocolchicine and the salts thereof have significant antitumor effects, are more active than paclitaxel, vincristine, and colchicine, do not exhibit cross resistance to the paclitaxel and the vincristine, and inhibit paclitaxel-resistant cell growth in vivo. With in vivo acceptable therapeutic indexes, the methylaminocolchicine and the salts thereof have a synergistic antitumor effect when used in combination with an anti-apoptotic protein Bcl-2/Bcl-xL inhibitor.

BRIEF DESCRIPTION OF THE DRAWINGS

FIG. 1A illustrates tumor growth curves after medication, FIG. 1B illustrates tumor weights at the end of the test, and FIG. 1C illustrates mouse weights after medication.

DETAILED DESCRIPTION OF THE EMBODIMENTS

Figure 1A:
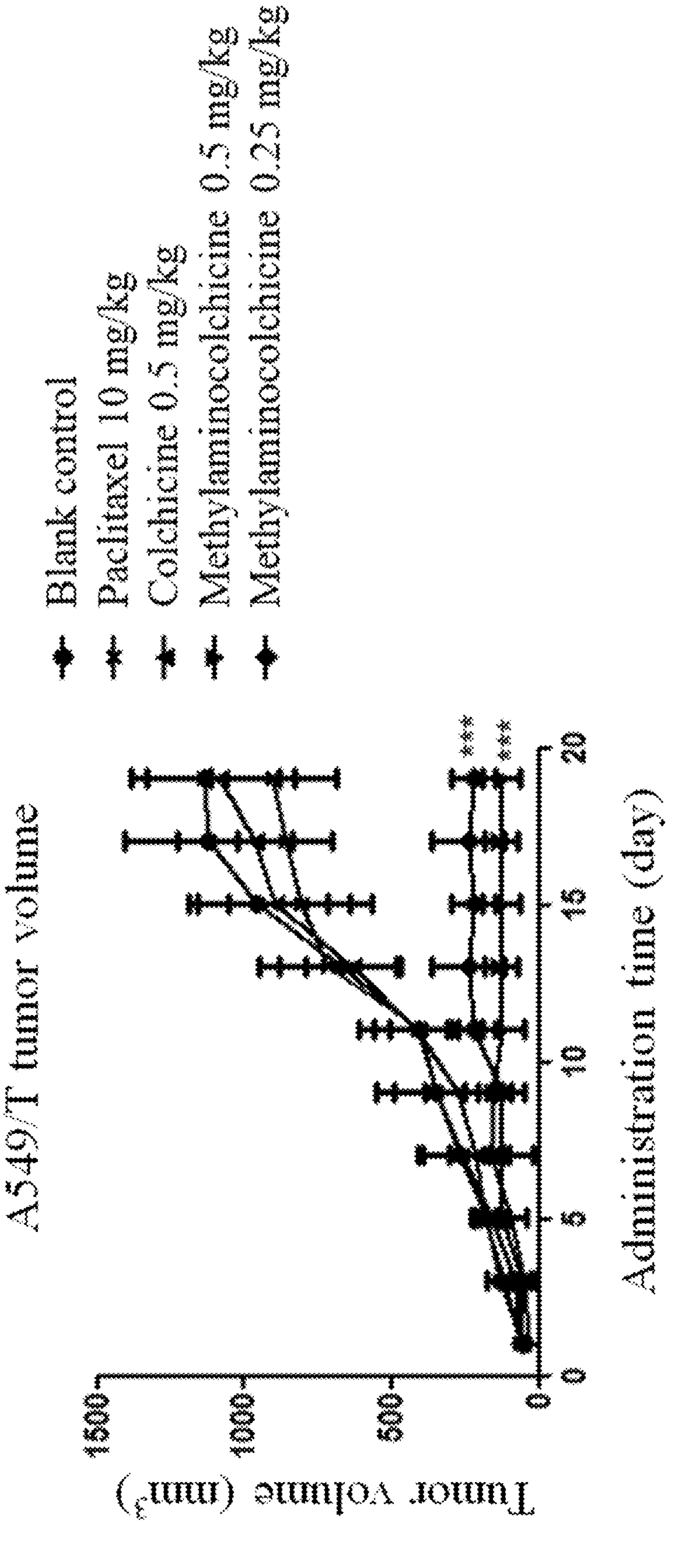
FIGS. 1A-1C illustrate the tumor growth inhibition effect of methylaminocolchicine provided by an example of the present disclosure in BALB/c-nu mice, where
Figure 1B:
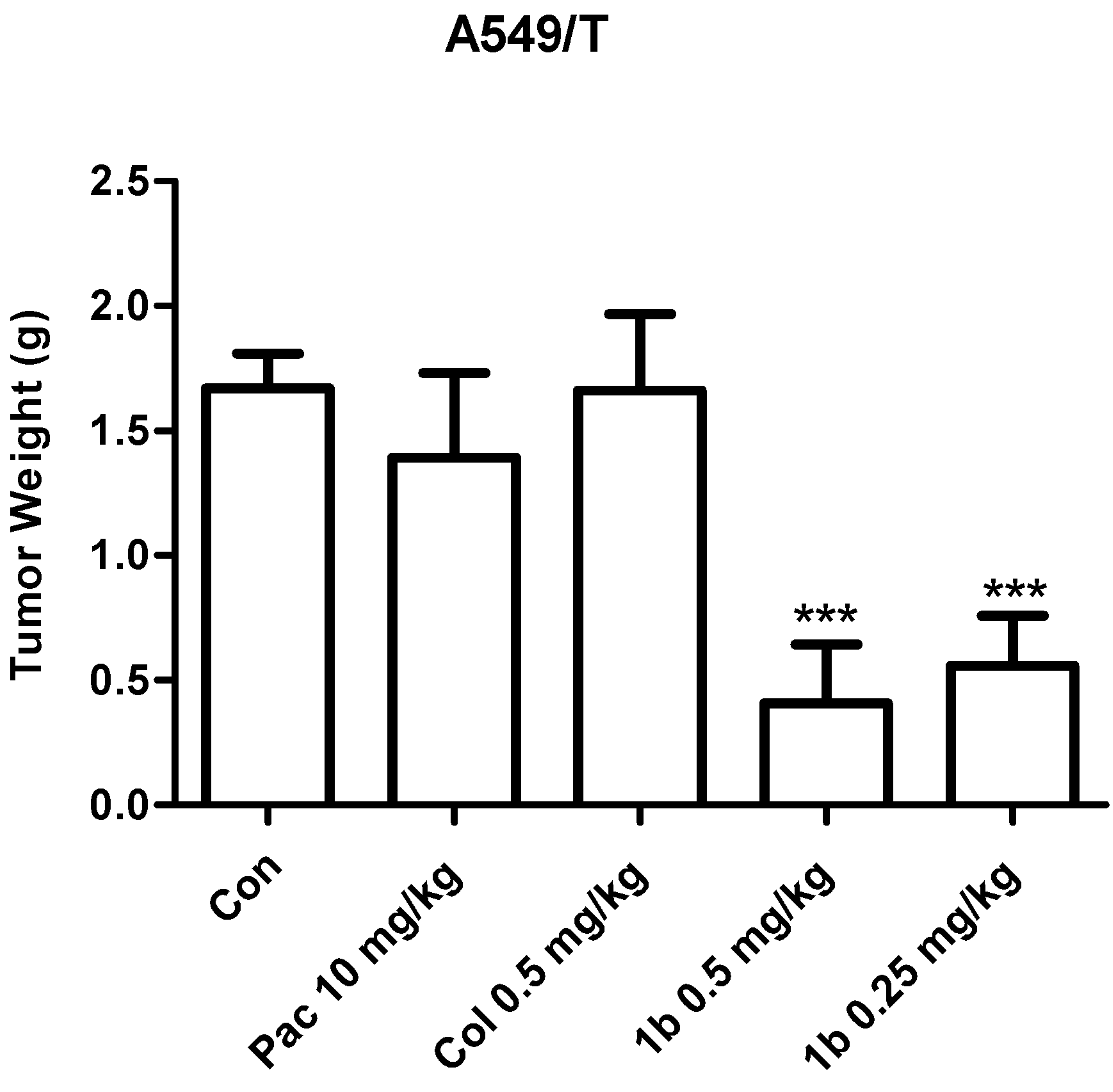

The substantive content of the present disclosure will be further described below in conjunction with examples, but they do not limit the protection scope of the present disclosure.

Example 1. Preparation of Methylaminocolchicine

Reaction Equation

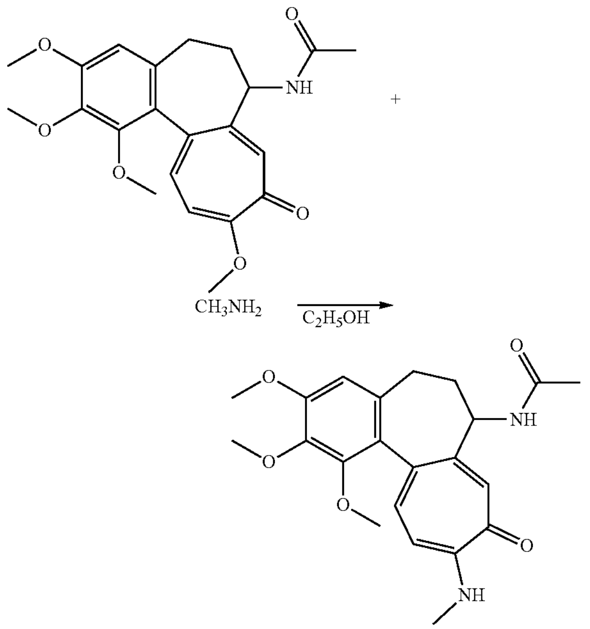

Operation Procedure:

Colchicine (1.5 g, 3.8 mmol, 1 eq) was added to a reactor and reacted with methylamine in alcohol (10 mL) at 80° C. for 10 h. Post-treatment: The reaction mixture was evaporated to dryness to obtain 1.4 g of yellow powdery solid, with a yield of 90.36%. ESI-MS: 399.1 $[M+H]^+$

Example 2. Methylaminocolchicine Hydrochloride

Reaction Equation:

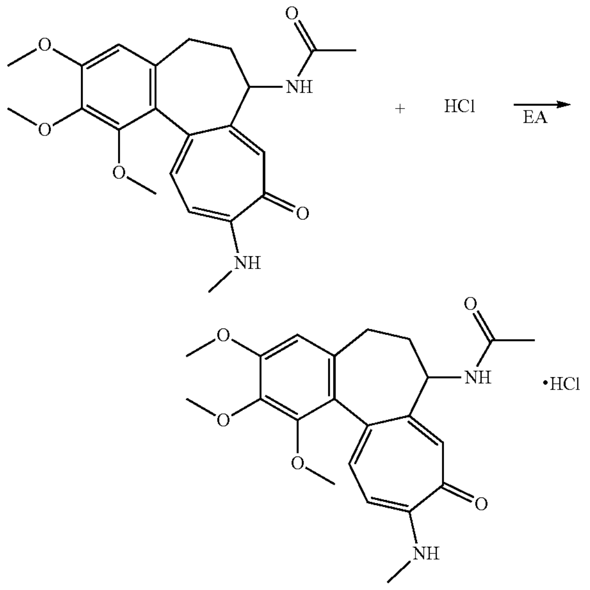

Operation Procedure:

Methylaminocolchicine (150 mg, 0.4 mmol, 1 eq) was added to a 25 mL single-mouth flask and dissolved in ethyl acetate (EA) (5 mL). At 0° C., HCl in EA (0.5 mL) was slowly added dropwise, and large amount of yellow precipitates were separated out of the reaction mixture.

Post-Treatment:

After suction filtration under reduced pressure, the filter cake was washed with EA (10 mL) and dried to obtain 155 mg of yellow powdery solid. $^{1}$HNMR (400 MHZ, DMSO-d6) δ8.61 (d, J=7.0 Hz, 1H), 8.21 (s, 1H), 7.38-7.32 (m, 2H), 6.83-6.80 (m, 1H), 6.77 (s, 1H), 4.37-4.31 (m, 1H), 3.83 (s, 3H), 3.79 (s, 3H), 3.49 (s, 3H), 3.01 (s, 3H), 2.56-2.53 (m, 1H), 2.20-2.02 (m, 2H), 1.91-1.90 (m, 1H), and 1.88 (s, 3H).

Example 3. Preparation of Methylaminocolchicine Sulfate

Reaction Equation:

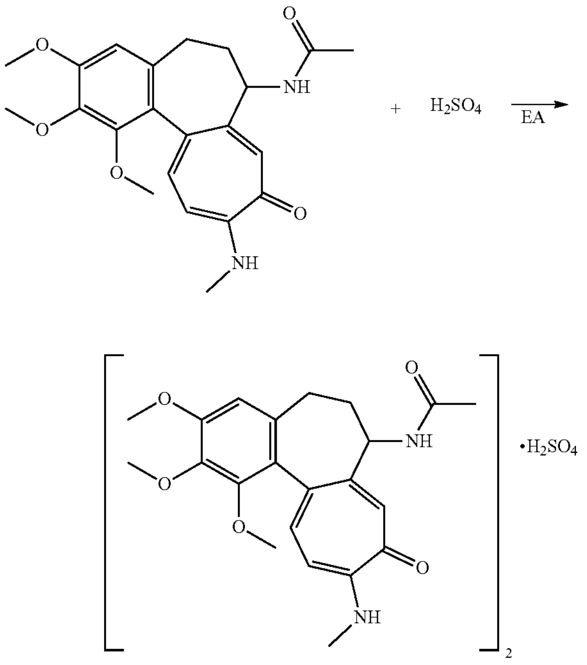

Operation Procedure:

Methylaminocolchicine (150 mg, 0.4 mmol, 1 eq) was added to a 25 mL single-mouth flask and dissolved in EA (5 mL). At 0° C., $H_2SO_4$ in EA (0.5 mL) was slowly added dropwise, and large amount of yellow precipitates were separated out of the reaction mixture.

Post-Treatment:

After suction filtration under reduced pressure, the filter cake was washed with EA (10 mL) and dried to obtain 138 mg of yellow powdery solid. 1HNMR (400 MHZ, DMSO-d6) δ8.59 (d, J=6.9 Hz, 1H), 8.44 (s, 1H), 7.46 (d, J=11.5 Hz, 1H), 7.35 (s, 1H), 6.95 (d, J=11.5 Hz, 1H), 6.79 (s, 1H), 4.36-4.30 (m, 1H), 3.84 (s, 3H), 3.79 (s, 3H), 3.50 (s, 3H), 3.04 (s, 3H), 2.58-2.54 (m, 1H), 2.19-2.07 (m, 2H), 1.94-1.93 (m, 1H), and 1.88 (s, 3H).

Example 4. Preparation of Methylaminocolchicine Mesylate

Reaction Equation:

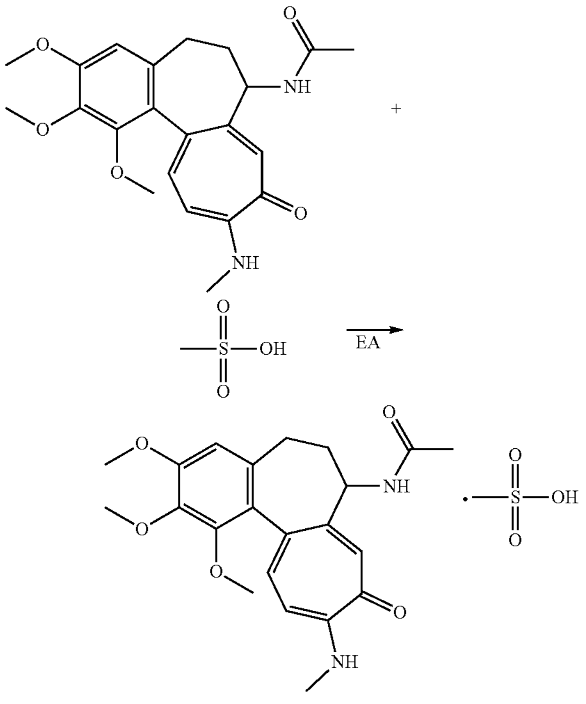

Operation Procedure:

Methylaminocolchicine (150 mg, 0.4 mmol, 1 eq) was added to a 25 mL single-mouth flask and dissolved in EA (5 mL). In a salt-ice bath at −10° C., methanesulfonic acid in EA (0.5 mL) was slowly added dropwise, and large amount of yellow precipitates were separated out of the reaction mixture.

Post-Treatment:

After suction filtration under reduced pressure, the filter cake was washed with EA (10 mL). The filter cake changed from a solid to a yellow oily matter, which was evaporated to dryness under reduced pressure to obtain 165 mg of yellow powdery solid.

Example 5. Preparation of Methylaminocolchicine p-Toluenesulfonate

Reaction Equation:

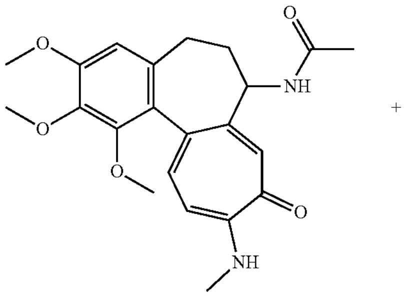

-continued

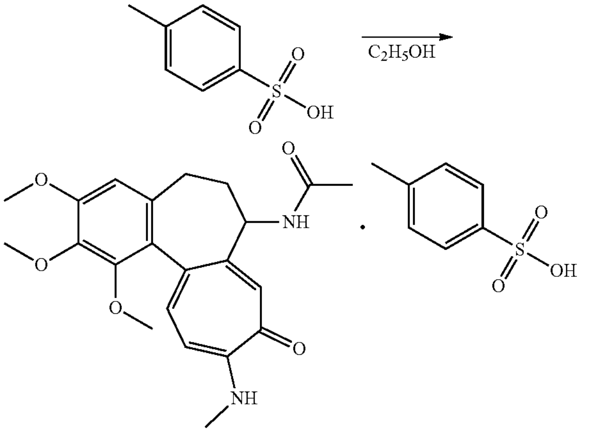

Operation Procedure:

Methylaminocolchicine (150 mg, 0.4 mmol, 1 eq) was added to a 25 mL single-mouth flask and dissolved in ethanol (5 mL). At 0° C., p-toluenesulfonic acid (70 mg, 0.4 mmol, 1 eq) in ethanol (5 mL) was slowly added dropwise, and the reaction was conducted at room temperature for 3 h. Post-treatment: After suction filtration, the filter cake was dried to obtain 168 mg of yellow powdery solid. 1HNMR (400 MHZ, DMSO-d6) δ8.60 (d, J=6.8 Hz, 1H), 8.44 (s, 1H), 7.50-7.45 (m, 3H), 7.36-7.35 (m, 1H), 7.12 (d, J=7.9 Hz, 2H), 6.97-6.95 (m, 1H), 6.79 (s, 1H), 4.36-4.30 (m, 1H), 3.84 (s, 3H), 3.79 (s, 3H), 3.50 (s, 3H), 3.04 (s, 3H), 2.59-2.54 (m, 1H), 2.29 (s, 3H), 2.16-2.08 (m, 2H), 1.94-1.90 (m, 1H), and 1.87 (s, 3H).

Example 6. Preparation of Methylaminocolchicine Tartrate

Reaction Equation:

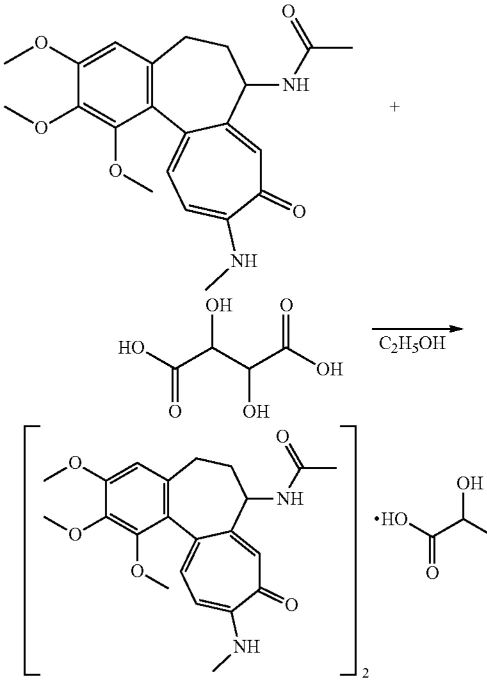

Operation Procedure:

Methylaminocolchicine (150 mg, 0.4 mmol, 1 eq) was added to a 25 mL single-mouth flask and dissolved in ethanol (5 mL). In a salt-ice bath at −10° C., tartaric acid (30 mg, 0.2 mmol, 0.5 eq) in ethanol (5 mL) was slowly added dropwise, and the reaction mixture was transferred for reaction at room temperature for 3 h.

Post-Treatment:

After suction filtration, the filter cake was dried to obtain 165 mg of yellow powdery solid. $^1$HNMR (400 MHz, DMSO-d6) δ8.53 (d, J=7.7 Hz, 1H), 7.81-7.77 (m, 1H), 7.20 (d, J=11.1 Hz, 1H), 7.08 (s, 1H), 6.74 (s, 1H), 6.56 (d, J=11.4 Hz, 1H), 4.41-4.34 (m, 1H), 4.30 (s, 1H), 3.82 (s, 3H), 3.78 (s, 3H), 3.48 (s, 3H), 2.96 (d, J=5.2 Hz, 3H), 2.56-2.54 (m, 1H), 2.22-2.14 (m, 1H), 2.07-1.99 (m, 1H), and 1.86-1.83 (m, 4H).

Example 7. The Growth Inhibition Activity of Methylaminocolchicine Against Tumor Cells Human acute myeloid leukemia cells HL-60, human chronic myeloid leukemia cells K562, human prostate cancer cell line PC-3, human hepatoma cells HepG-2, human colon cancer cells HC-T116, and human cervical cancer cell line Hela were purchased from American Type Culture Collection (ATCC). Human acute myeloid leukemia cells MOLM-13 were purchased from DSMZ-Deutsche Sammlung von Mikroorganismen und Zellkulturen GmbH (Braunschweig Germany).

Methylaminocolchicine and colchicine were each weighed accurately and dissolved in dimethyl sulfoxide (DMSO) to prepare 1 mM stock solutions, which were stored at −20° C. and diluted with absolute alcohol to an appropriate concentration to serve as test solutions when in use.

MOLM-13, HL-60, K562, PC-3, HCT-116, and Hela cells were each cultured in 1640 Medium, and HepG-2 cells were cultured in Dulbecco's Modified Eagle Medium (DMEM) supplemented with 10% inactivated fetal bovine serum (FBS), 10 mmol/L L-glutamine, 100 U/mL penicillin, and 100 μg/mL streptomycin. All cells were cultured in a 37° C., 5% $CO_2$ and saturated humidity incubator.

Cell Growth Inhibition Assay

Suspension cells: Leukemia cells HL-60, MOLM-13, and K562 were inoculated into a 24-well plate at a density of 0.5-1×$10^5$ cells/mL. Subsequently, the cells were incubated with different concentrations of compounds in an incubator for 72 h. Then, the culture plate was removed from the incubator. In each well, the cells and the compounds were mixed well; 50 μL of cell suspension was transferred and mixed well with 50 μL of Trypan Blue (0.4%), followed by counting microscopically.

Cell growth inhibition rate was calculated according to the following formula. The growth inhibition rate $GI_{50}$ (the concentration that results in inhibiting cell growth by 50%) was calculated by GraphPadPrism5.

Growth inhibition rate=(1−Cell count of the drug group/Cell count of the control group)×100%.

Adherent cells: PC-3, HepG-2, HCT-116, and Hela cells were inoculated into a 96-well plate at a density of 1,000-3,500 cells/mL. After incubation overnight, 100 μL of culture medium supplemented with various concentrations of compounds was added to each well. After incubation for 96 h, 50 μL of methyl thiazolyl tetrazolium (MTT) solution (2 mg/mL) was added to each well and incubated at 37° C. for 4 h. The culture medium was suctioned, and the cells were dissolved in 200 μL of DMSO. The absorbance at 570 nm was measured by using a microplate reader. The growth inhibition rate $GI_{50}$ was calculated by GraphPadPrism5.

TABLE 1

$GI_{50}$ values of the growth inhibition of methylaminocolchicine and colchicine against tumor cells

| Cancer type | Cell line | $GI_{50}$ ± SD (nM) Colchicine | Methylamino-colchicine |
|---|---|---|---|
| Leukemia | HL-60 | 9.30 ± 3.70 | 3.50 ± 0.14 |
| | K562 | 10.70 ± 1.50 | 5.00 ± 0.32 |
| | MOLM-13 | 11.56 ± 1.21 | 4.87 ± 0.86 |
| Prostatic cancer | PC-3 | 90.54 ± 25.16 | 9.19 ± 0.81 |
| Liver cancer | HepG-2 | 57.68 ± 5.41 | 7.05 ± 1.74 |
| Colorectal cancer | HCT-116 | 79.33 ± 6.59 | 9.16 ± 4.19 |
| Cervical carcinoma | Hela | 124.11 ± 8.41 | 9.97 ± 2.34 |

Methylaminocolchicine had significant growth inhibitory effects on hematological tumor cells (MOLM-13, HL-60, and K562), prostate cancer cells PC-3, hepatoma cells HepG-2, colon cancer cells HCT-116, and cervical cancer cells Hela and was more active than colchicine.

Example 8 Growth Inhibition Activity of Methylaminocolchicine Against Resistant Tumor Cells The cells used in the assay included human NSCLC A549 cells and paclitaxel-resistant A549/T cells, human breast cancer MCF-7 cells and paclitaxel-resistant MCF-7/T cells, human breast cancer MX-1 cells and paclitaxel-resistant MX-1/T cells, and human oral epidermoid carcinoma KB cells and vincristine-resistant KB/V cells.

A549 and A549/T cells were cultured in 1640 Medium, while MX-1, MX-1/T, MCF-7, MCF-7/T, KB, and KB/V cells were cultured in DMEM supplemented with 10% inactivated FBS, 10 mmol/L L-glutamine, 100 U/mL penicillin, and 100 μg/mL streptomycin in a 37° C., 5% $CO_2$ and saturated humidity incubator.

Pharmaceutical formulation and activity assay were carried out with reference to those in Example 7.

TABLE 2

$GI_{50}$ values of methylaminocolchicine, paclitaxel, vincristine, and colchicine against four pairs of resistant cells $GI_{50}$ ± SD (nM)

| | Paclitaxel | Vincristine | Colchicine | Methylaminocolchicine |
|---|---|---|---|---|
| A549 | 23.06 ± 1.39 | 45.63 ± 3.68 | 38.35 ± 3.37 | 6.88 ± 0.67 |
| A549/T | 4755 ± 75 | 1128.96 ± 12.69 | 1083.4 ± 2.37 | 23.64 ± 0.06 |
| RI | 209.45 | 24.7 | 28.25 | 3.44 |
| MCF-7 | 57.95 ± 9.62 | 158.92 ± 44.57 | 51.38 ± 10.75 | 20.7 ± 2.80 |
| MCF-7/T | 941.13 ± 265.08 | 576.48 ± 80.69 | 251.26 ± 61.02 | 47.59 ± 2.82 |
| RI | 16.24 | 3.63 | 4.89 | 2.3 |
| KB | 3.52 ± 0.95 | 2.69 ± 1.53 | 10.89 ± 1.26 | 6.41 ± 2.39 |
| KB/V | 603.62 ± 28.59 | 268.48 ± 13.13 | 88.77 ± 9.83 | 36.30 ± 6.77 |
| RI | 171.48 | 99.68 | 8.15 | 4.29 |
| MX-1 | 67.30 ± 5.92 | 16.66 ± 6.87 | 57.94 ± 7.55 | 11.18 ± 1.17 |
| MX-1/T | 1125.76 ± 228.32 | 262.15 ± 6.80 | 838.19 ± 2.62 | 11.36 ± 1.20 |
| RI | 16.73 | 14.47 | 15.74 | 1.02 |

RI: resistance index. The value is the calculated ratio of the $GI_{50}$ of the resistant cells to that of parental cells.

RI: resistance index. The value is the calculated ratio of the $GI_{50}$ of the resistant cells to that of parental cells.

From Table 2, in parental cells, colchicine has similar growth inhibition ability to paclitaxel and vincristine. In four parental cell lines, methylaminocolchicine has better anti-proliferation effect than colchicine, paclitaxel, and vincristine. Paclitaxel and vincristine exhibit cross resistance in the above four resistant tumor cell lines. Methylaminocolchicine exhibit minimum cross resistance to paclitaxel or vincristine in the above four pairs of cell lines. In A549 and A549/T cells, the resistance index of methylaminocolchicine is only 3, whereas that of colchicine is about 28. In MX-1 and MX-1/T cells, the resistance index of methylaminocolchicine is only 1, whereas that of colchicine is about 15.

Example 9 In Vivo Inhibition of Methylaminocolchicine Against Paclitaxel-Resistant Cell Growth Male BALB/c-nu mice (aged 6-8 weeks and weighing 18-20 g) were purchased from Beijing HFK Bioscience Co., Ltd. A549/T cells in logarithmic growth phase were mixed with Matrigel, and inoculated subcutaneously in the right armpit of a BALB/c-nu mouse at a density of $5\times10^6$ cells/mouse. When the mean tumor volume reached 50-80 $mm^3$, nude mice were randomly divided into five groups: (1) blank control group; (2) colchicine (0.5 mg/kg) group; (3) paclitaxel (10 mg/kg); (4) methylaminocolchicine (0.25 mg/kg); and (5) methylaminocolchicine (0.5 mg/kg). Colchicine and methylaminocolchicine were dissolved in DMSO: normal saline (1:9), paclitaxel was formulated into a DMSO/PEG400/Tween 80/normal saline (1:4:0.5:4.5) solution, and administered intraperitoneally every other day, for 10 times.

The mental state of the mice was monitored every day. The mouse weight was measured and recorded, and mouse weight change curves were plotted based on the average body weight of each group. The long and short diameters of tumors were measured every two days, and the tumor volume was calculated according to the tumor volume calculation formula: tumor volume=(long diameter×short diameter$^2$)/2. Tumor growth curves were plotted (FIG. 1A).

Figure 1C:
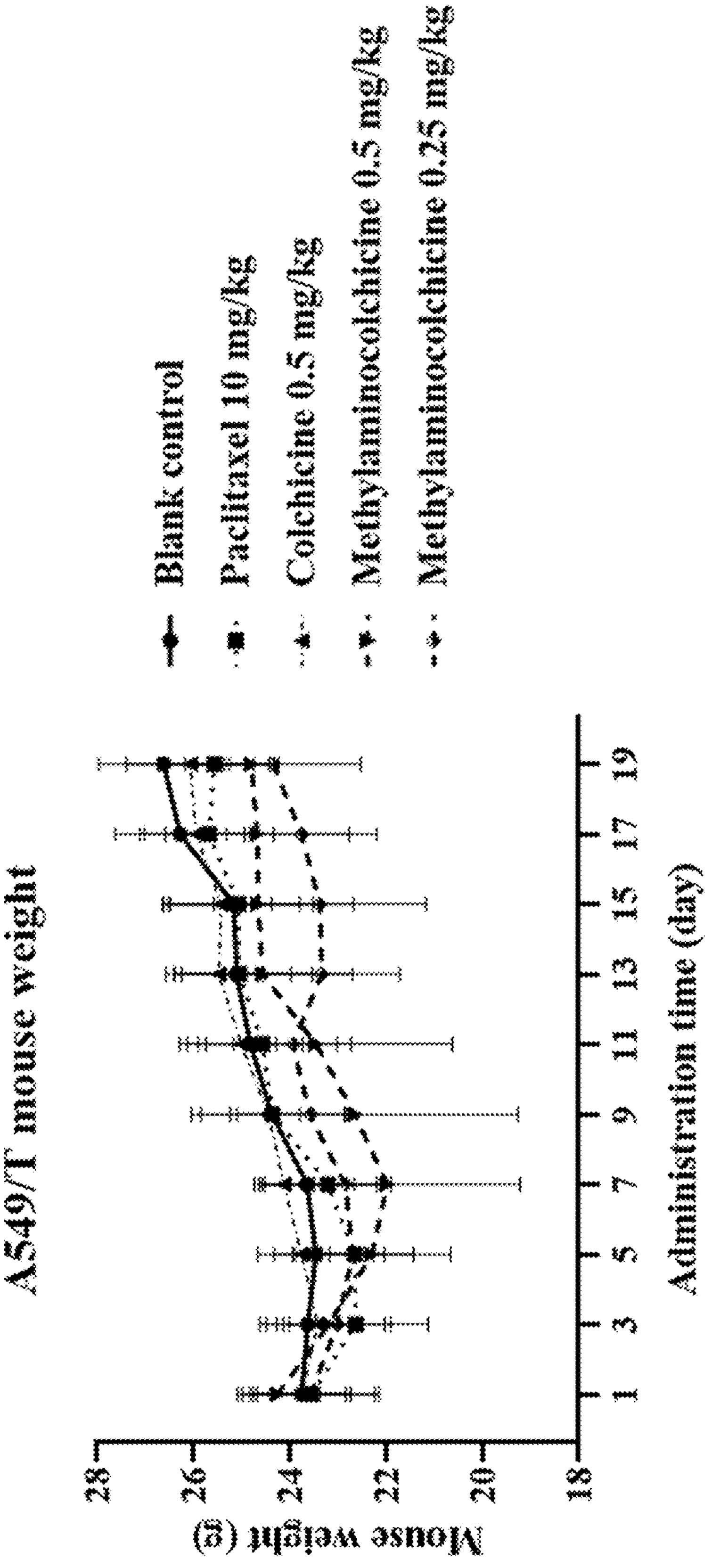

From FIG. 1C, there is no significant change in mouse weight throughout the assay. In A549/T xenograft models, neither paclitaxel nor colchicine can significantly inhibit the tumor growth, but methylaminocolchicine can.

Example 10 Promotion of Microtubule Polymerization by Methylaminocolchicine

Figure 2:
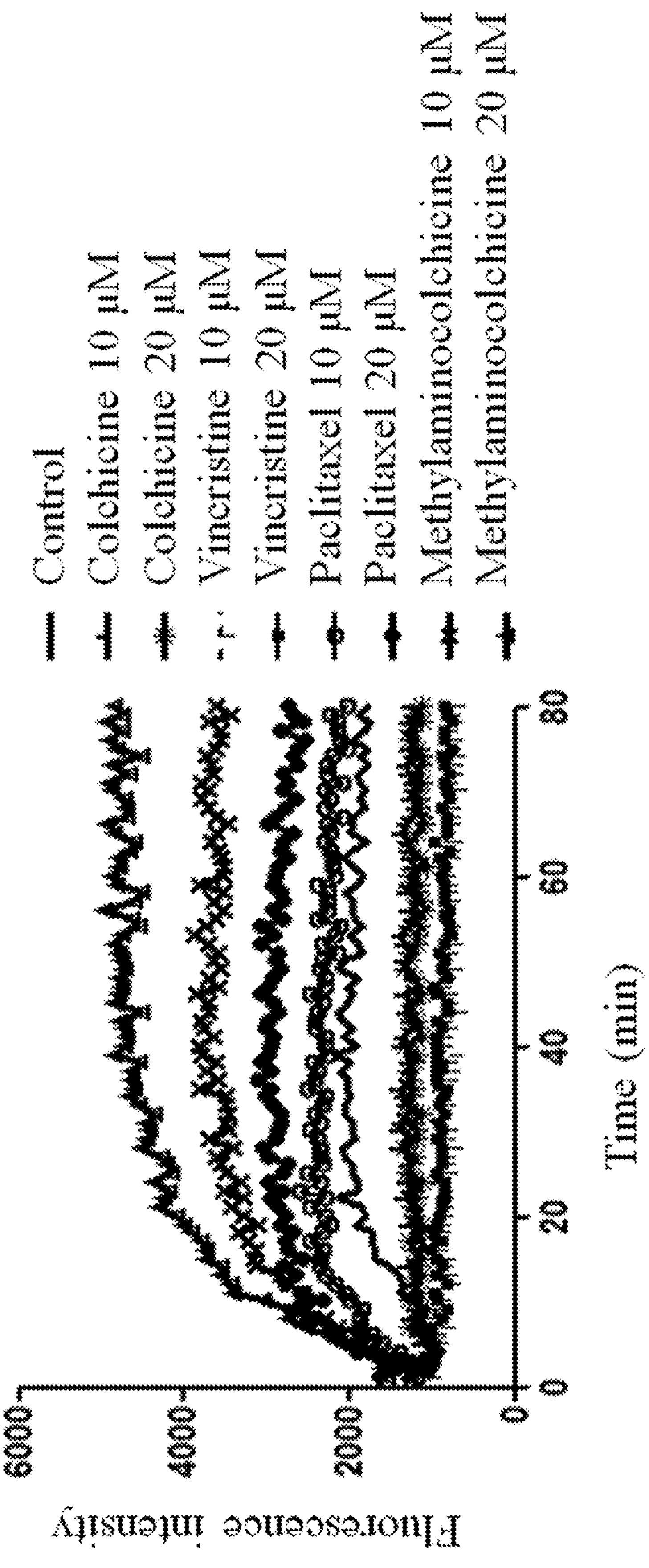
FIG. 2 illustrates the effects of methylaminocolchicine, paclitaxel, vincristine, and colchicine provided by an example of the present disclosure on microtubule polymerization force.

In vitro tubulin polymerization assay was carried out using purified tubulin. BK011P-Tubulin Polymerization Assay Kit (Cytoskeleton, Denver, CO) was used. Porcine brain tubulin solution (2 mg/mL) was prepared by using tubulin buffer (80 mM PIPES, 2.0 mM $MgCl_2$, 0.5 mM EGTA, 15% v/v glycerol, and 1 mM GTP). Tubulin solution was mixed with methylaminocolchicine, colchicine, and paclitaxel solution in a 96-well plate and incubated in a Varioskan Flash Multimode Reader at 37° C. Fluorescence intensities (ex-360 nm, em-450 nm) was measured and monitored every 1 min, for consecutive 80 min (FIG. 2).

It has been known that paclitaxel promotes tubulin polymerization and vincristine inhibits it. Therefore, both of them were selected as control drugs. Methylaminocolchicine, colchicine, vincristine, and paclitaxel were each used at concentrations of 10 and 20 μM. Like vincristine, colchicine could inhibit tubulin polymerization. Contrary to the action of colchicine, methylaminocolchicine promoted tubulin polymerization and had better efficacy than paclitaxel (FIG. 2). Methylaminocolchicine promoted tubulin polymerization in a unique way, unlike the mode of action of colchicine inhibiting the tubulin polymerization.

Example 11 Growth Inhibition Activity of Methylaminocolchicine Salts Against Resistant and Non-Resistant Tumor Cells Cell lines used in the assay included human NSCLC A549 cells and paclitaxel-resistant A549/T cells. Cell culture, drug preparation, and activity assay were carried out with reference to those in Examples 3 to 7.

Different methylaminocolchicine salts were each weighed accurately and dissolved in DMSO to prepare 1 mM stock solutions, which were stored at −20° C. and diluted with absolute alcohol to an appropriate concentration to serve as test solutions when in use.

TABLE 3

$GI_{50}$ values of methylaminocolchicine salts against A549 and A549/T cells

| Compound | $GI_{50}$ (nM) A549 | $GI_{50}$ (nM) A549/T | RI |
|---|---|---|---|
| Methylaminocolchicine hydrochloride | 16.89 | 63.68 | 3.77 |
| Methylaminocolchicine sulfate | 21.90 | 42.40 | 1.94 |
| Methylaminocolchicine mesylate | 16.96 | 29.86 | 1.76 |
| Methylaminocolchicine tartrate | 16.25 | 32.35 | 1.99 |
| Methylaminocolchicine p-toluenesulfonate | 18.27 | 72.68 | 3.98 |

RI: resistance index. The value is the calculated ratio of the $GI_{50}$ of the resistant cells to that of parental cells.

RI: resistance index. The value is the calculated ratio of the $GI_{50}$ of the resistant cells to that of parental cells.

From Table 3, in A549 and A549/T cells, methylaminocolchicine salts have tumor cell growth inhibitory effects comparable to methylaminocolchicine, and their resistance indexes are less than 5.

Example 12 Concomitant Medication of Methylaminocolchicine and Anti-Apoptotic Protein Bcl-2/Bcl-xL Inhibitors (Venetoclax, Navitoclax, A1331852, and A1155463) Synergizes the Antitumor Effect Cells used in the assay were paclitaxel-resistant A549/T cells. Cell culture and activity assay were carried out with reference to those in Example 7. The combination index (CI) of the pharmaceutical composition was calculated by Compusyn software.

Methylaminocolchicine, venetoclax, navitoclax, A1331852, and A1155463 were each weighed accurately and dissolved in DMSO to prepare 20 mM stock solutions, which were stored at −20° C. and diluted with absolute alcohol to an appropriate concentration to serve as test solutions when in use.

A549/T cells were each treated with 20-80 nM methylaminocolchicine in combination with 5-20 μM venetoclax, navitoclax, A1331852, and A1155463 for 96 h.

TABLE 4

Synergistic inhibition of A549/T cell growth by a combination of methylaminocolchicine and venetoclax

| Methylaminocolchicine (nM) | Venetoclax (μM) | Growth inhibition rate (%) | Combination index CI |
|---|---|---|---|
| 20 | — | 1.00 | — |
| 40 | — | 1.00 | — |
| 80 | — | 34.48 | — |
| — | 5 | 23.16 | — |
| — | 10 | 57.66 | — |
| — | 20 | 95.53 | — |
| 20 | 5 | 35.30 | 1.01 |
| 20 | 10 | 75.23 | 0.95 |
| 20 | 20 | 95.17 | 0.88 |
| 40 | 5 | 65.50 | 0.66 |
| 40 | 10 | 83.38 | 0.81 |
| 40 | 20 | 96.07 | 0.82 |
| 80 | 5 | 76.05 | 0.62 |
| 80 | 10 | 86.92 | 0.78 |
| 80 | 20 | 96.07 | 0.85 |

TABLE 5

Synergistic inhibition of A549/T cell growth by a combination of methylaminocolchicine and navitoclax

| Methylaminocolchicine (nM) | Navitoclax (μM) | Growth inhibition rate (%) | Combination index CI |
|---|---|---|---|
| 20 | — | 1.00 | — |
| 40 | — | 3.08 | — |
| 80 | — | 42.77 | — |
| — | 5 | 2.84 | — |
| — | 10 | 67.66 | — |
| — | 20 | 96.34 | — |
| 20 | 5 | 35.82 | 0.82 |
| 20 | 10 | 80.39 | 0.84 |
| 20 | 20 | 96.39 | 1.00 |
| 40 | 5 | 76.32 | 0.57 |
| 40 | 10 | 88.98 | 0.75 |
| 40 | 20 | 96.36 | 1.03 |
| 80 | 5 | 79.99 | 0.68 |
| 80 | 10 | 90.78 | 0.81 |
| 80 | 20 | 96.39 | 1.08 |

TABLE 6

| Synergistic inhibition of A549/T cell growth by a combination of methylaminocolchicine and A1331852 | | | |
|---|---|---|---|
| Methylaminocolchicine (nM) | A1331852 (μM) | Growth inhibition rate (%) | Combination index CI |
| 20 | — | 1.00 | — |
| 40 | — | 1.00 | — |
| 80 | — | 37.66 | — |
| — | 5 | 5.17 | — |
| — | 10 | 11.18 | — |
| — | 20 | 17.47 | — |
| 20 | 5 | 7.28 | 1.34 |
| 20 | 10 | 17.69 | 0.66 |
| 20 | 20 | 21.53 | 0.80 |
| 40 | 5 | 11.59 | 1.04 |
| 40 | 10 | 21.36 | 0.70 |
| 40 | 20 | 35.47 | 0.48 |
| 80 | 5 | 47.29 | 0.43 |
| 80 | 10 | 58.28 | 0.34 |
| 80 | 20 | 69.31 | 0.26 |

TABLE 7

| Synergistic inhibition of A549/T cell growth by a combination of methylaminocolchicine and A1155463 | | | |
|---|---|---|---|
| Methylaminocolchicine (nM) | A1155463 (μM) | Growth inhibition rate (%) | Combination index CI |
| 20 | — | 1.00 | — |
| 40 | — | 0.97 | — |
| 80 | — | 38.92 | — |
| — | 5 | 6.97 | — |
| — | 10 | 12.13 | — |
| — | 20 | 23.67 | — |
| 20 | 5 | 3.61 | 1.71 |
| 20 | 10 | 26.65 | 0.69 |
| 20 | 20 | 66.53 | 0.42 |
| 40 | 5 | 15.16 | 0.91 |
| 40 | 10 | 65.89 | 0.31 |
| 40 | 20 | 71.01 | 0.43 |
| 80 | 5 | 58.91 | 0.42 |
| 80 | 10 | 72.69 | 0.37 |
| 80 | 20 | 76.35 | 0.46 |

From Tables 4, 5, 6, and 7, when treated with 20-80 nM methylaminocolchicine, 5-20 μM venetoclax, 5-20 μM navitoclax, 5-20 μM A1331852, and 5-20 μM A1155463 alone for 96 h, the growth of less than 50% of cells is inhibited. The addition of methylaminocolchicine can significantly enhance cell growth inhibitory effects of venetoclax, navitoclax, A1331852, and A1155463. Combination indexes of two drugs are calculated by Compusyn software. The combination index between methylaminocolchicine and each of venetoclax, navitoclax, A1331852, and A1155463 is less than 1, indicating the synergism between two compounds. The combination index between methylaminocolchicine and A1155463 is minimal, indicating the strongest synergism between the two compounds.

What is claimed is:

1. A method for treating a tumor or a tumor resistant to a microtubule inhibitor, the method comprising administering to subject in need thereof medicament comprising methylaminocolchicine or a salt thereof, alone or in combination with an anti-apoptotic protein inhibitor:

wherein the methylaminocolchicine or the salt thereof comprises a methylamino substitution at the C10 position of colchicine;

wherein the methylaminocolchicine is represented by Formula I:

Formula I

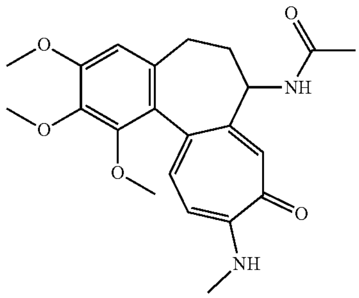

the salt thereof is represented by Formula II:

Formula II

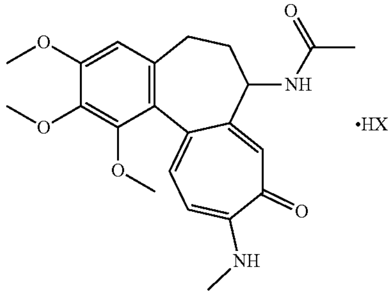

wherein HX is selected from the group consisting of hydrochloric acid, hydrobromic acid, nitric acid, sulfuric acid, phosphoric acid, sulfamic acid, trifluoroacetic acid, acetic acid, benzoic acid, methanesulfonic acid, phenylacetic acid, salicylic acid, oxalic acid, maleic acid, malic acid, fumaric acid, succinic acid, tartaric acid, lactic acid, gluconic acid, hydroxymaleic acid, and 1,4-butanedisulfonic acid;

wherein the tumor is a hematological malignancy and/or a solid tumor; and wherein the tumor is selected from the group consisting of leukemia, prostatic cancer, liver cancer, colorectal cancer, cervical carcinoma, breast cancer, lung cancer, renal cancer, gastric cancer, and skin cancer; and wherein the anti-apoptotic protein inhibitor is a Bcl-2 inhibitor or a Bcl-xL inhibitor.

2. The method according to claim 1, wherein the methylaminocolchicine and the salts thereof are in a pharmaceutical dosage form of a tablet, a capsule, a granule, and an injection.

3. The method according to claim 1, wherein the medicament comprising the methylaminocolchicine or the salts thereof are administered concomitantly, or in sequentially in any order with the anti-apoptotic protein inhibitor.

4. The method according to claim 1, wherein the medicament comprising the methylaminocolchicine and the salts thereof further comprises a pharmaceutically acceptable carrier or vehicle and is formulated into a clinically acceptable preparation.

* * * * *